United States Patent [19]
Eldred et al.

[11] 4,128,629
[45] Dec. 5, 1978

[54] EXTRACTION-FREE CORTISOL ASSAY

[75] Inventors: Emmet W. Eldred, North Attleboro; Hubert J. P. Schoemaker, Newton, both of Mass.

[73] Assignee: Corning Glass Works, Corning, N.Y.

[21] Appl. No.: 812,992

[22] Filed: Jul. 5, 1977

[51] Int. Cl.$^2$ ............................................. G01N 33/16
[52] U.S. Cl. ...................................... 424/1; 23/230 B; 424/12
[58] Field of Search ............................ 424/7, 12, 105; 23/230 B

[56] References Cited
U.S. PATENT DOCUMENTS
4,034,073  7/1977  Weetall .................................... 424/1

OTHER PUBLICATIONS

Brombacher et al., Journal of Endocrinology, vol. 72, No. 1, Jan. 1977, p. 57P.
Tilden, Clinical Chemistry, vol. 23, No. 2, Feb. 1977, pp. 211–215.
Farmer et al., Clinical Chemistry, vol. 20, No. 4, Apr. 1974, pp. 411–414.
Foster et al., Clinical Chemistry, vol. 20, No. 3, Mar. 1974, pp. 365–368.

Primary Examiner—Benjamin R. Padgett
Assistant Examiner—Christine M. Nucker
Attorney, Agent, or Firm—Clinton S. Janes, Jr.; William E. Maycock; Clarence R. Patty, Jr.

[57] ABSTRACT

Immobilization of active anti-cortisol antibodies onto negatively charged solid phase surfaces results in a shift of the antibody pH optimum to an acidic range thereby permitting effective yet minimal use of deblocking agents and an extraction-free immunoassay for cortisol.

8 Claims, 4 Drawing Figures

EXTRACTION-FREE CORTISOL ASSAY

BACKGROUND OF THE INVENTION

1. Field:

This disclosure is concerned generally with an analytical method for determining very small concentrations of a substance in a liquid. More specifically, the disclosure is concerned with an immunoassay for cortisol.

2. Prior Art:

The term immunoassay (IA) refers to methods for determining the presence or concentration of a substance in a fluid which methods require, at some point, the complexation of an antibody and a substance (antigen or hapten) to which the antibody is specific. Since it is known that antibodies to a given substance tend to be very specific to that substance, that specificity has been employed in a variety of immunoassay techniques to determine the presence or concentration of substances which are present in very small quantities in human body fluids such as blood.

Typically, an immunoassay is based on a competition between molecules of a given substance and similar molecules (which have been labeled) for a limited number of complexing sites on antibodies which are specific to the substance (both the unlabeled and labeled forms). After the competition for complexing sites, the complexed materials are separated from the reaction solution and the amount of label associated with the separated materials or the remaining solution is then quantitated. That quantitation can be related to previously prepared standards to determine the presence or amount of the unlabeled substance.

A variety of labels are known and used in immunoassays. For example, fluorogenic materials useful in a fluoroimmunoassay (FIA) are described in U.S. Pat. No. 3,940,475 to Gross. Enzyme labels can be coupled to antibodies or antigens to perform an enzyme immunoassay (EIA) as illustrated in U.S. Pat. No. 3,654,090 to Schuurs et al. Radioisotopes can be incorporated into an antibody or substance (antigen or hapten) to perform a radioimmunoassay (RIA) as described in U.S. Pat. No. 3,555,143 to Axen et al. As used herein, the expression labeled substance, label, marker, tracer, or the equivalent, includes any of those known labels.

As pointed out, an immunoassay requires, at some point, an immunochemical complexation between a substance and its antibody, one of which is labeled. By allowing a suitable incubation period during which labeled substances compete with, complex with, or displace unlabeled substances, and then quantitating the label (e.g. fluorometrically, enzymatically, radiometrically, etc.), it is possible to determine an unknown by known means.

Prior to such quantitation, however, it is necessary to separate the immunochemically complexed products (which must include at least some label) from the surrounding incubation medium (which includes the remaining label). Such separations can be facilitated by providing one of the complexing species in an immobilized (insolubilized) yet active form. For example, it is known that antigenic substances, haptens, or antibodies thereto can be attached to, or incorporated in, various water insoluble carrier materials without substantial loss of biological or immunochemical activity. See, for example, U.S. Pat. No. 3,555,143 (organic supports or carriers) and U.S. Pat. No. 3,652,761 (inorganic carriers). When either of the reactants in an immunoassay is used in such an immobilized form, there is present a solid phase which, when appropriate, can be readily separated (e.g. by centrifugation) for label quantitation. The use of composites comprising antibodies or antigens associated with or immobilized on essentially water insoluble carrier materials is commonly referred to as solid phase immunoassay (SPIA). The use of inorganic siliceous materials as antibody supports in solid phase radioimmunoassays (SPRIA) is described in detail in U.S. Pat. No. 3,975,511 to W. Vann et al.

A major problem in measuring the concentrations of substances present in serum is the interference of other materials which are present, often in much larger concentrations. Very commonly, the interference is due to proteins. It is known that certain interferring proteins sometimes can be inactivated by the use of chemicals known as deblocking agents without significantly affecting the antibody. See, for example, U.S. Pat. No. 3,911,096 to Chopra which discloses the use of deblocking agents such as 8-anilino-1-naphthalene sulfonic acid (ANS) and related compounds for immunoassays (non-SPIA) of throid hormones. Unfortunately, it has been found that when some deblocking agents are used in effective amounts in some IA systems, the antibodies lose part of their activity. This has tended to discourage the use of known deblocking agents in some systems, specifically those systems in which the antibody and interferring protein are inactivated to similar degrees by the deblocking agents.

The desirability of being able to accurately determine cortisol concentrations in human body fluids (e.g. serum) is well known. Cortisol is the major glucocorticoid produced and secreted by the adrenal cortex and its presence affects many body functions. Hence, the determination of cortisol concentration has been found helpful in the diagnosis and treatment of a variety of human ailments. Because the clinically significant concentration range of cortisol is very small (e.g. about 12.5 to 800 ng/ml), cortisol concentrations are commonly determined via immunoassay techniques.

In blood serum, there exist several cortisol binding proteins which can interfere with a cortisol immunoassay. The most commonly cited interfering protein is the protein transcortin (TC). Although transcortin is present in relatively low concentrations, it has a fairly high binding capability for cortisol. Hence, to assure accuracy in any assay for cortisol, it is necessary to eliminate or at least minimize the interfering effects of TC and other cortisol binding proteins, collectively referred to herein as TC.

The use of deblocking agents to assure the release of cortisol from TC had not met with significant success because the deblocking agents also tended to inactivate the cortisol antibodies. Hence, TC removal or inactivation, has tended to require the use of laborious and time-consuming extraction steps or heat denaturation steps. These added steps are not only cumbersome, but also add to the possibility of erroneous results merely because of the added steps required.

Quite surprisingly, we have now developed an extraction-free immunoassay for cortisol which can be performed at room temperature. Details of our assay and preferred methods of performing it are described below.

SUMMARY OF THE INVENTION

Our immunoassay for determining the concentration of cortisol in a serum sample comprises the steps of:

(a) incubating the sample, labeled cortisol, and an effective deblocking agent in an aqueous medium with a composite comprising anti-cortisol antibodies fixed onto the surfaces of a negatively charged support material, the incubation being at a pH ranging from about 4.0 to 6.5 and being under conditions sufficient to result in the formation of immunochemical complexes on the composite, some of which complexes include labeled cortisol;

(b) separating the composite from the incubation medium;

(c) determining the amount of label on the separated composite or in the remaining incubation medium; and (d) relating the determination of step (c) to a standard to determine the cortisol concentration in the sample.

In preferred embodiments, the anti-cortisol antibodies are fixed onto the surfaces of high surface area siliceous particles and the deblocking agent is ANS.

SPECIFIC EMBODIMENTS

Our discovery is based in part on the observation that when anti-cortisol antibodies are immobilized in active form onto the surfaces of certain negatively charged support surfaces, the optimum pH range of the antibodies tends to shift from the normal range of about 7.0 to 8.0 to an acidic range of 4.0 to 6.5. At the lower pH value the antibodies function as well as at the higher pH value before being immobilized. This phenomenon is thought to be due to a change in the microenvironment of the antibodies and it can be used in concert with known deblocking agents to avoid TC extraction or heat-denaturation steps in a cortisol immunoassay. At the lower pH (more acidic) the TC is already partially inactivated and only a relatively small concentration of deblocking agent is needed to make the assay free from TC interferences.

Figure 1:
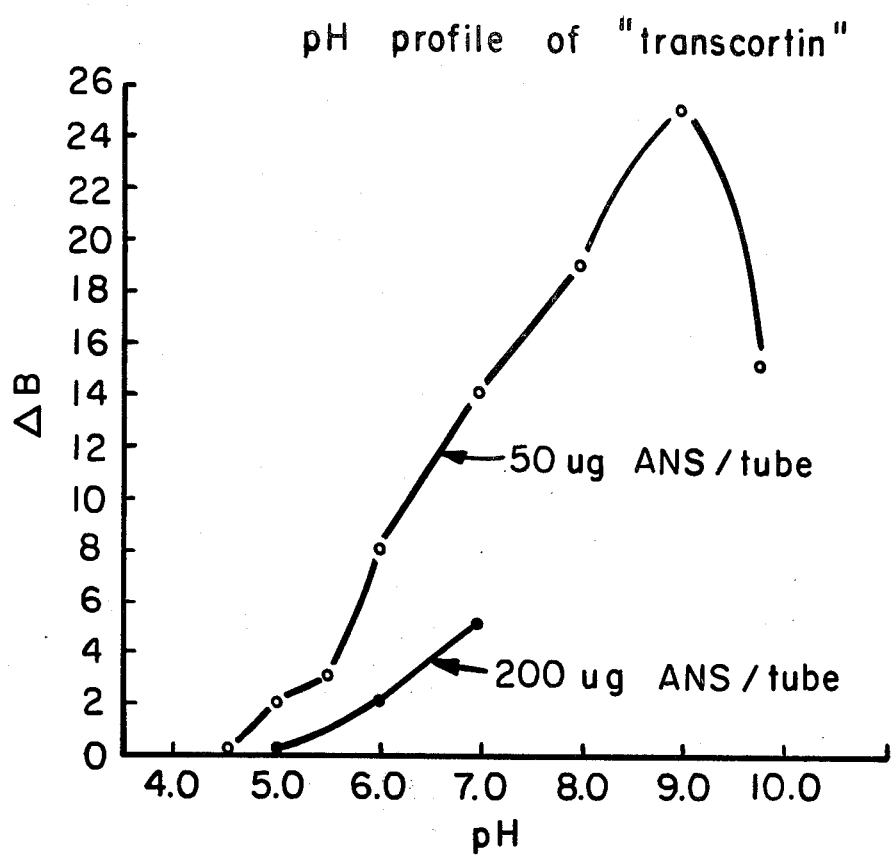
FIG. 1 is a graph illustrating the pH profile for "transcortin" or TC.
Figure 2:
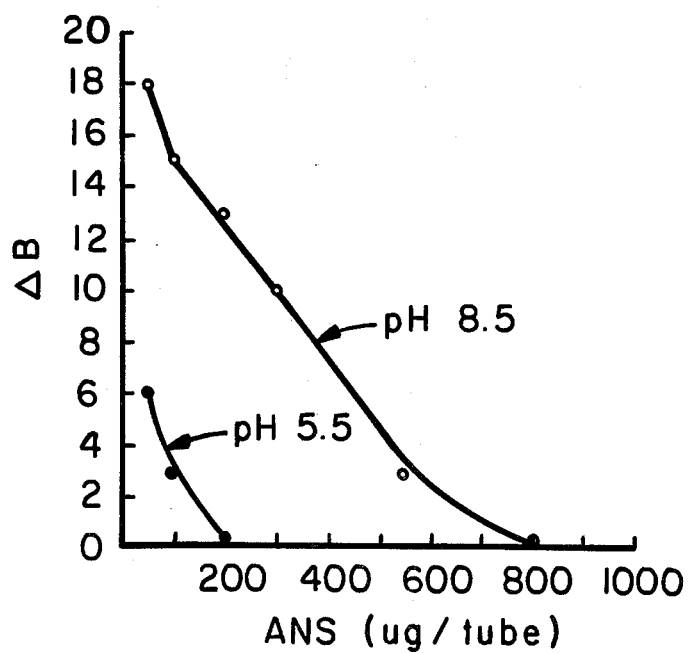
FIG. 2 is a graph illustrating the TC interferring effect at various ANS concentrations at pH 5.5 and pH 8.5.
Figure 3:
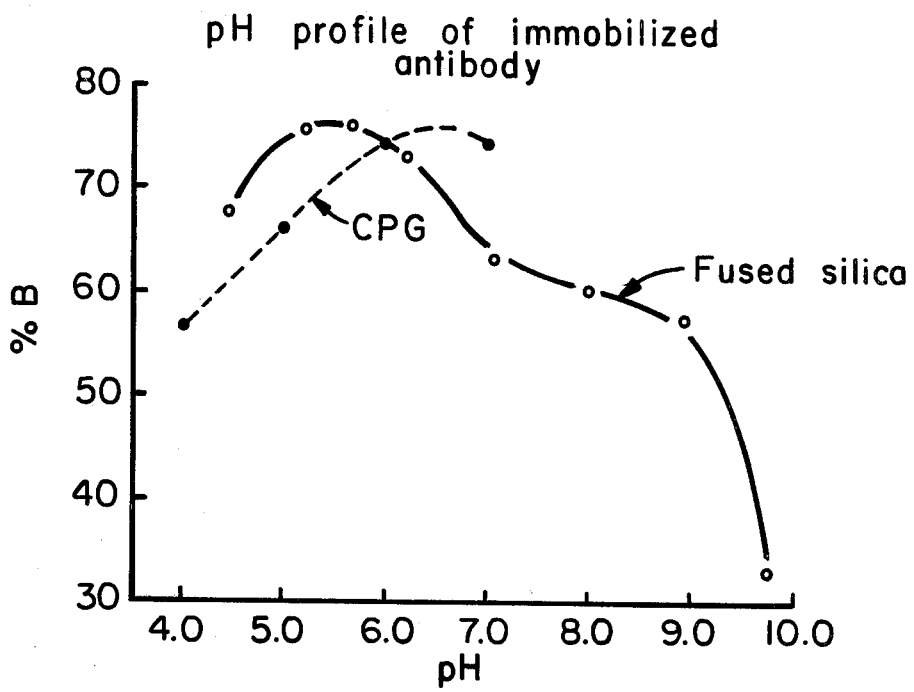
FIG. 3 is a graph illustrating the pH optimum of immobilized anti-cortisol antibodies using siliceous carriers.

The overall basis of our discovery can be seen in FIGS. 1, 2, and 3. In FIGS. 1 and 2, $\Delta B$ is a measure of the TC interferring effect in cortisol immunoassays and represents the percent binding (%B) of cortisol in the absence of TC minus the %B of cortisol in the presence of TC. As can be seen in FIG. 1, the pH optimum of the TC or "transcortin" (transcortin per se plus related cortisol binding substances) is clearly in the alkaline range (pH optimum about 8–9). This means that the further the pH in the reaction mixture is from that pH, the less interference there will be due to TC binding.

FIG. 2 illustrates the binding of cortisol to TC at different concentrations of deblocking agents at pH 5.5 and pH 8.5. As can be seen, less ANS was needed at the lower pH. This is a beneficial effect in that, unfortunately, deblocking agents such as ANS tend to slightly inactivate antibodies. Thus, it is an advantage to use as little deblocking agent as possible to release the cortisol.

FIG. 3 illustrates the pH optimum obtained using the antibody supports of this disclosure. In FIG. 2, CPG represents controlled pore glass. As can be seen, the optimum shifts from the normal 7.0 to 8.0 physiological pH range to a somewhat abnormal range of pH 4.0 to about 6.5 when the siliceous supports are used. This occurs without lowering the antibody binding capacity for cortisol. This phenomenon, in concert with the fact that TC has an alkaline pH optimum permits the use of relatively small amounts of deblocking agents which have minimal adverse effects on the antibody system (because of the small amounts which can be used effectively). Thus, it can be said that the combined results of FIGS. 1, 2, and 3 form the overall basis of our invention. An effective deblocking agent can be readily determined by one skilled in the art and the best effective amount can be determined experimentally as was done by us to generate the data for FIG. 2.

In very preferred embodiments, our negatively charged antibody support materials comprise siliceous materials such as finely divided particles of fused silica or porous glass (e.g. CPG). For reasons disclosed in detail in U.S. Pat. No. 3,975,511 to Vann et al., a preferred support particle size ranges from about 0.7 to 3.0 microns. That particle size range permits suspendibility of the ultimate composite during the incubation step, thus assuring maximum exposure of reactants. That particle size range also allows the use of commonly available centrifuges to separate the composites. The main requirement for the support is that it have a negatively charged surface such that when the anti-cortisol antibodies are attached thereto, there results a shift in the pH optimum to an acidic range (less than 7.0). A very high surface area per unit weight is very desirable to assure maximum antibody loading and this can be satisfied by using particulate supports, finely divided.

Although the antibodies may be attached or fixed on the carrier supports via a variety of methods such as by simple adsorption or by chemical (covalent) means, in very preferred embodiments, the antibodies are bonded to siliceous supports via intermediate silane coupling agents. The use of these coupling agents to attach a wide variety of biologically active materials (e.g. antibodies, antigens, enzymes, coenzymes, etc.) to inorganic surfaces is well known. In the examples below the supports consisted of silanized porous glass and silanized fused silica.

The blocking agents are those which will function well in an acidic environment. The main requirements for the deblocking agents are that they tend to adversely affect (inactivate) the TC more so than the immobilized anti-cortisol antibodies in an acidic pH, especially in the range of pH 4.0 to 6.5. Deblocking agents of the type which meet those requirements are described in U.S. Pat. No. 3,911,096, to Chopra. Our preferred deblocking agents are ANS and related compounds described therein.

Although any suitable label which can be associated with or incorporated into the cortisol molecule may be used, we prefer the use of radioisotope labels because of their current use and the high degree of assay sensitivity which results from their use. Our labeled cortisol, also referred to as the tracer, consisted of a $I^{125}$ labeled tyramine derivative of cortisol, prepared by known means, which can be disposed of via the normal sewer system.

Our overall assay consists of four basic steps: an initial incubation step, a separation step, a label quantitation step, and a correlation step. Unlike most other assays, only three pipetting steps are needed, thus reducing possibility of operator error. The incubation step can be completed in one hour at room temperature, a clear advantage. As shown in the standard curve below, the assay has a proven sensitivity ranging from 12.5 ng/ml to about 800 ng/ml, easily covering the clinically significant ranges for serum cortisol, both AM and PM.

A very preferred method of performing our assay is described in the Example below.

EXAMPLE

A lyophilized mixture of the tracer (about 50,000 DPM), 200 μg of ANS, and PBS is reconstituted to a 100 μl solution with water in an identified glass test tube to which is pipetted a 25 μg serum sample having an unknown cortisol concentration. A non-interferring red dye such as Durkees Staff Brand may be included with the tracer solution to indicate that presence of the tracer.

Then, a 1 ml suspension of the immobilized antibodies (0.20 mg of anti-cortisol antibodies chemically coupled via N-hydroxysuccinimide linkage to silanized glass particles having an average particle size of about 1.7 microns is pipetted into the tube. The tube is vortexed for 2 or 3 seconds, allowing the composite of immobilized antibodies to be suspended. The reaction tube is incubated for about 1 hour at room temperature. The tube is then centrifuged for about 10 minutes at about 1400 to 1600 gravities (g). The relatively high density of the glass support facilitates this separation step. After centrifugation, the supernatant fluid is decanted and it or the composite at the bottom of the tube is counted for radioactivity. Since the amount of radioactivity in disintegrations per minute (DPM) of the initial tracer was known, the amount associated with the composite (that which competed with the unknown cortisol for sites on the composite), provides an indication of the cortisol present, using known correlation techniques.

Figure 4:
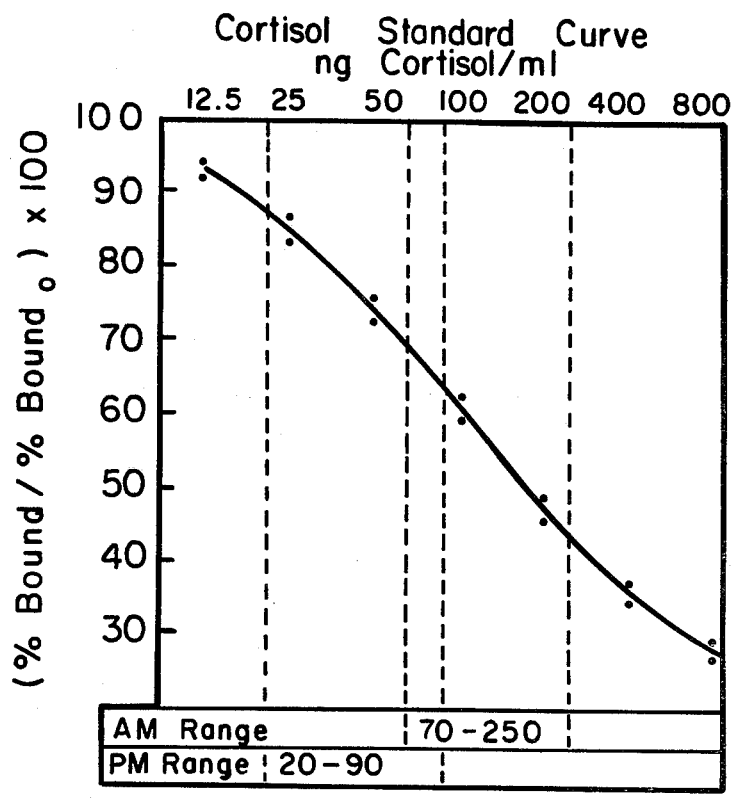
FIG. 4 is a graph illustrating a typical standard curve for a cortisol immunoassay.

To establish a standard curve for the correlation step, it is only necessary to plot the differences in % bound of labeled cortisol of known amounts against the known concentrations. Typical standards for "known" cortisol concentrations would be 0 ng/ml, 12.5 ng/ml, 25 ng/ml, 50 ng/ml, 100 ng/ml, 200 ng/ml, 400 ng/ml, and 800 ng/ml. Thus, by correlating the % bound (%B) of an unknown (as determined by DPM of bound tracer) with the same %B from the standard curve, the unknown concentration can be determined. In FIG. 4 the above technique was used but the %B for each standard was normalized to %B at the zero ng/ml standard, i.e.

$$\left( \frac{\%B \text{ standard } x}{\%B \text{ standard } o} \right) \times 100.$$

The $B/B_o$ plot is used routinely. The reliability of the method and the typical standard curve of FIG. 4 has been confirmed repeatedly with unknown serum samples and in clinical trials.

FURTHER EXPERIMENTS

The value of the blocking agents in releasing cortisol from TC is illustrated in the Table below where the amount of cortisol released from a serum sample by the ANS and pH is compared with the amount of cortisol released via a typical heating step which denatures TC. The heating step involved heating the serum sample at 100° C. for about 10 min. The Table illustrates typical patient cortisol values in ng/ml obtained by the two techniques.

TABLE I

| | Cortisol Released (ng/ml) | | | |
|---|---|---|---|---|
| ANS | 59 | 90 | 270 | 465 |
| Heating | 46 | 92 | 295 | 460 |

Specificity of the above assay

The cross-reactivity of the anticortisol antibody composite for a substance may be expressed as the ratio of the amount of cortisol required to displace 50% of the labeled antigen from the antibody, to the amount of cross-reacting substance needed to cause a similar displacement.

| Substance | Ratio of Cross Reactivity* |
|---|---|
| Cortisol | 1.00 |
| 11-Desoxycortisol | 0.11 |
| Tetrahydrocortisol | <0.001 |
| Cortisone | 0.008 |
| Corticosterone | 0.12 |
| 11-Desoxycorticosterone | 0.10 |
| Progesterone | 0.041 |
| 17α-Hydroxyprogesterone | 0.026 |
| 20β-Hydroxyprogesterone | 0.026 |
| Prednisone | 0.004 |
| Prednisolone | 0.10 |
| Estrone | <0.001 |
| Estradiol-17β | <0.001 |
| Estriol | <0.001 |
| Testosterone | 0.002 |
| 5α-Dihydrotestosterone | 0.007 |
| Androstenedione | <0.004 |
| Cholesterol | <0.001 |

*The results are expressed as the ratio of the cortisol level to the steroid level at fifty percent relative displacement.

The above results illustrate a high degree of specificity for our immobilized anti-cortisol composites.

Accuracy of the Assay

Experiments to measure the recovery of known amounts of cortisol from defibrinated, charcoal-extracted plasma samples have shown recovery to be from 98% to 107%. Some of the results exceeded 100% because of experimental errors such as exact addition of weight-out cortisol, precision error and dilution errors. As a guide-line, recovery values between 90 and 110% are considered excellent in this field.

| Initial Cortisol Level (ng/ml) | Cortisol Added (ng/ml) | Measured Cortisol (ng/ml) | Percent Recovery |
|---|---|---|---|
| 0 | 35 | 34.2 | 98% |
| 0 | 100 | 105.2 | 105% |
| 0 | 200 | 214.2 | 107% |
| 0 | 300 | 299.7 | 100% |
| 0 | 400 | 395.2 | 99% |
| 35 | 40 | 77 | 103% |
| 35 | 75 | 110 | 100% |
| 35 | 500 | 550 | 103% |
| 35 | 750 | 770 | 98% |

In preferred embodiments, very small amounts of preservatives such as sodium azide or merthiolate may be added to the lyophilized reagents to prevent biological growth.

Since it is thought that the above described solid phase immunoassay is subject to numerous variations, it is intended that the above described examples should be deemed illustrative only and that the scope of the present invention should be limited only by the following claims.

We claim:

1. An immunoassay for determining the concentration of cortisol in a serum sample, the assay comprising the steps of:
   (a) incubating the sample, labeled cortisol, and an effective amount of deblocking agent in an aqueous medium with a composite comprising anti-cortisol antibodies fixed onto the surfaces of a negatively charged support material, the incubation being at a pH ranging from about 4.0 to about 6.5 and being under conditions sufficient to result in the formation of immunochemical complexes on the composite, some of which complexes include labeled cortisol;
   (b) separating the composite from the incubation medium;
   (c) determining the amount of label on the separated composite or in the remaining incubation medium; and
   (d) relating the determination of step (c) to a standard to determine the cortisol concentration in the sample.

2. The assay of claim 1 wherein the antibodies are fixed onto the surfaces of siliceous particles.

3. The assay of claim 1 wherein the siliceous particles are silanized siliceous particles.

4. The method of claim 1 wherein the deblocking agent is 8-anilino-1-naphthalene sulfonic acid, or a salt thereof.

5. The method of claim 1 wherein the incubation step is for a period of less than about one hour.

6. The method of claim 1 wherein all steps are performed at room temperature.

7. The method of claim 1 wherein the labeled cortisol comprises a $I^{125}$ tyramine derivative of cortisol.

8. The method of claim 1 wherein the serum sample size is about 25 microliters.